(12) United States Patent
ElAttrache et al.

(10) Patent No.: US 8,012,174 B2
(45) Date of Patent: Sep. 6, 2011

(54) METHOD FOR DOUBLE ROW FIXATION OF TENDON TO BONE

(75) Inventors: Neal S. ElAttrache, Los Angeles, CA (US); James E. Tibone, Los Angeles, CA (US)

(73) Assignee: Arthrex, Inc., Naples, FL (US)

( * ) Notice: Subject to any disclaimer, the term of this patent is extended or adjusted under 35 U.S.C. 154(b) by 854 days.

(21) Appl. No.: 11/700,916

(22) Filed: Feb. 1, 2007

(65) Prior Publication Data

US 2007/0191849 A1  Aug. 16, 2007

Related U.S. Application Data

(60) Provisional application No. 60/763,915, filed on Feb. 1, 2006.

(51) Int. Cl.
*A61F 17/04* (2006.01)
*A61F 2/08* (2006.01)
(52) U.S. Cl. ..................... 606/232; 623/13.11
(58) Field of Classification Search .......... 606/224–233; 623/13.11–13.14, 22.36, 23.27
See application file for complete search history.

(56) References Cited

U.S. PATENT DOCUMENTS

| 7,083,637 | B1 * | 8/2006 | Tannhauser | 606/228 |
| 2003/0125739 | A1 * | 7/2003 | Bagga et al. | 606/61 |
| 2004/0093030 | A1 * | 5/2004 | Cox et al. | 606/232 |
| 2004/0193217 | A1 * | 9/2004 | Lubbers et al. | 606/232 |
| 2005/0089552 | A1 * | 4/2005 | Altman et al. | 424/445 |
| 2006/0004364 | A1 * | 1/2006 | Green et al. | 606/72 |
| 2006/0074422 | A1 * | 4/2006 | Story et al. | 606/72 |
| 2006/0079904 | A1 | 4/2006 | Thal | |

* cited by examiner

*Primary Examiner* — Suzette J Gherbi
(74) *Attorney, Agent, or Firm* — Dickstein Shapiro LLP (57) ABSTRACT

A system and method for soft tissue to bone repair employing at least one suture anchor combined with at least one knotless fixation device. The method for soft tissue to bone fixation includes: (i) providing a first medial row constructed with a first plurality of fixation devices, at least one of the first plurality of fixation devices is an anchor; and (ii) providing a second lateral row constructed with a second plurality of fixation devices, at least one of the second plurality of fixation devices is a knotless fixation device, and suture or tape or allograft/biological component extending over the soft tissue and secured in place by the anchors in the first and second medial rows.

29 Claims, 9 Drawing Sheets

METHOD FOR DOUBLE ROW FIXATION OF TENDON TO BONE

CROSS-REFERENCE TO RELATED APPLICATIONS

This application claims the benefit of U.S. Provisional Application No. 60/763,915, filed Feb. 1, 2006, the entire disclosure of which is incorporated by reference herein.

FIELD OF THE INVENTION

The present invention relates to methods of arthroscopic surgery and, more specifically, to an improved method of attaching tissue to bone, such as rotator cuff repair.

BACKGROUND OF THE INVENTION

When soft tissue tears away from bone, reattachment becomes necessary. Various devices, including sutures, screws, staples, wedges, anchors and plugs have been used in the prior art to secure soft tissue to bone. Surgical methods utilizing suture anchors alone are disadvantageous for reattachment of large areas of detached tissue because they often do not allow good tissue to bone contact.

Reattachment of soft tissue to bone typically requires the surgeon to pass suture material through selected tissue, form a plurality of surgical knots extracorporeally and then move the knots into position adjacent the desired tissue to be sutured. In such procedures, the surgeon must manually tie the knots on the suture strands after the suture is threaded through the selected tissues to be sutured. Knot tying during surgery, particularly arthroscopic surgery, is tedious and time-consuming. There is also a tendency for the knots to deform or collapse as the surgeon manually forces the knots down into the proper position. Also, the suture knots often are exposed to abrasion or cutting by sharp or rough areas along the walls of the bone canal into which anchors are typically inserted to provide fixation of tendon to bone.

Accordingly, a need exists for an improved method for attaching soft tissue to bone which does not require multiple suture knots and which allows the tendon to remain securely in place until the ligaments naturally attach to bone. A method of threading suture through a tendon with maximum suture fixation strength, as well as a method of securing the tendon to bone that allows for accelerated tendon healing to bone are also needed.

BRIEF SUMMARY OF THE INVENTION

The present invention provides a system and method for soft tissue to bone repair employing at least one suture anchor combined with at least one knotless fixation device.

More specifically, the present invention provides a method for tendon to bone fixation which includes: (i) providing a first medial row constructed with a first plurality of fixation devices, at least one of the first plurality of fixation devices being an anchor; (ii) providing a second lateral row constructed with a second plurality of fixation devices, at least one of the second plurality of fixation devices being a knotless fixation device; and (iii) providing a structure comprising an element selected from the group consisting of suture, tape and allograft/biological component, and extending the structure over the soft tissue so that the structure is secured in place by the anchors.

Other features and advantages of the present invention will become apparent from the following description of the invention, which refers to the accompanying drawings.

DETAILED DESCRIPTION OF THE INVENTION

Referring now to the drawings, where like elements are designated by like reference numerals, FIGS. 1 through 15 illustrate systems and methods of attaching a tendon to bone according to the present invention. For exemplary purposes only, the invention will be described below with reference to an arthroscopic rotator cuff repair. However, the invention is not limited to this exemplary embodiment and has applicability to any reattachment of soft tissue to bone.

The methods of the present invention enhance footprint compression and allow for accelerated tendon healing to bone that is achieved with minimal knot tying. The repair consists of a tied medial row constructed with at least one suture anchor combined with knotless lateral fixation using at least one knotless fixation device. Preferably, the repair consists of a tied medial row constructed with two suture anchors (such as two Arthrex 5.5 mm Bio-Corkscrew® FT anchors, for example) combined with knotless lateral fixation using at least one knotless fixation device, preferably at least two knotless fixation devices (such as two Arthrex 3.5 mm Push-Lock™ anchors, two Arthrex SwiveLock™ anchors, a combination of the PushLock™ and SwiveLock™ anchors, or a combination of at least one of a PushLock™ and SwiveLock™ anchor with another knotless fixation device or with other fixation device, among others). The result is a quick, secure and low profile repair with excellent contact between tendon and bone.

Figure 1:
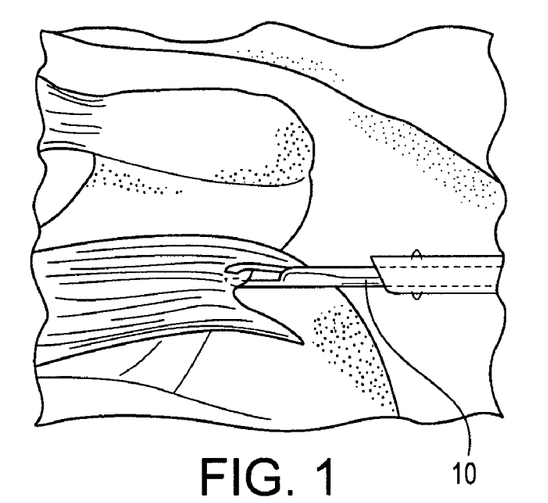
FIG. 1 is a side view illustrating an initial step of a method of arthroscopic rotator cuff repair according to an exemplary embodiment of the present invention.

FIG. 1 illustrates a side view of a human shoulder of a patient undergoing a rotator cuff repair in accordance with an exemplary embodiment of the present invention. Although this particular embodiment will be illustrated below with reference to FIGS. 1-10 and with reference to only a particular knotless fixation device (such as Arthrex "PushLock" anchor), the invention is not limited to this particular embodiment and contemplates additional embodiments wherein any knotless fixation device may be employed, depending on the characteristics of the repair site and of the particular application.

The patient may be positioned in the beach chair position using the Arthrex Beach Chair Lateral Traction Device or in a lateral decubitus position using the Arthrex 3-Point Shoulder Distraction System. Access to the subacromial space is facilitated with a variety of cannulas.

First, and as illustrated in FIG. 1, the mobility of the tear is assessed using, for example, a tissue grasper 10 such as the Arthrex KingFisher™ Suture Retriever/Tissue Grasper, to determine whether a U or L-shaped component exists. Where large tears extend to the superior aspect of the glenoid, margin convergence suturing is performed to reduce volume and strain on the repair. Subsequently, the length and width of the rotator cuff footprint is assessed and a bleeding bed for enhanced tendon to bone healing may be formed. This may be accomplished with a burr to perform a light dusting of the greater tuberosity, or by using a chondro pick to microfracture the footprint and maximize vascular channels.

Figure 2:
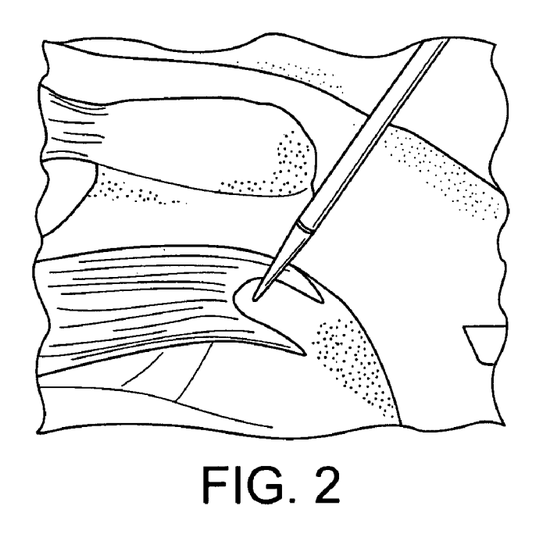
FIG. 2 is a side view of the structure of FIG. 1 and at a step subsequent to that shown in FIG. 1.

FIG. 2 illustrates the preparation of two pilot holes for two suture anchors that will be inserted in the medial row. A punch may be employed adjacent to the articular margin of the humerus and at about 45° angle to form the two pilot holes.

Figure 3:
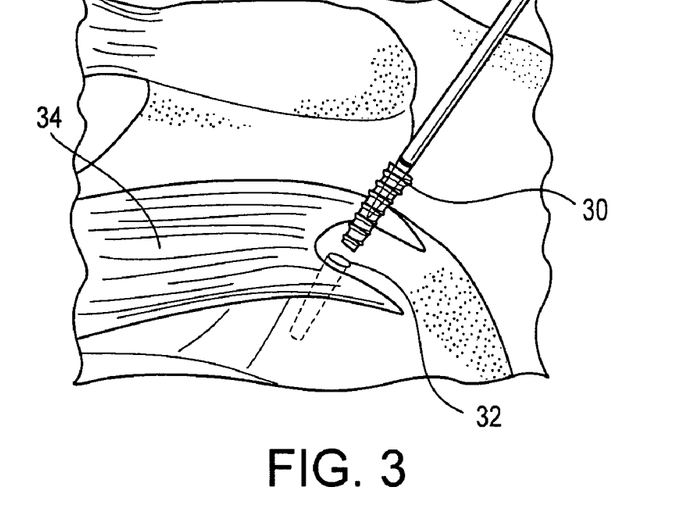
FIG. 3 is a side view of the structure of FIG. 1 and at a step subsequent to that shown in FIG. 2.
Figure 4:
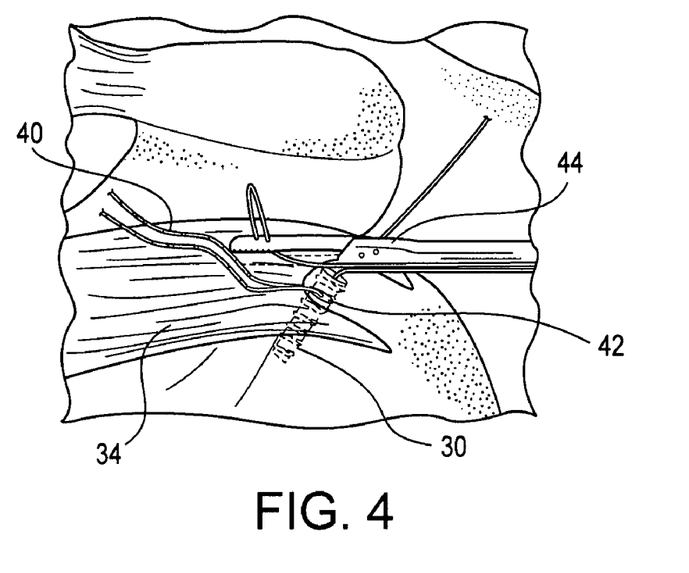
FIG. 4 is a side view of the structure of FIG. 1 and at a step subsequent to that shown in FIG. 3.

Subsequent to the formation of the pilot holes, and as shown in FIG. 3, a suture anchor 30 is placed in the pre-formed hole 32. As shown in FIG. 4, two suture anchors 30 are placed in the two pre-formed holes 32 in a medial row. These anchors assure full contact of the detached tendon 34 along the medial footprint of the greater tuberosity. In an exemplary embodiment, at least one of the two suture anchors is a fully-threaded bioabsorbable suture anchor having a loop inserted into the suture anchor, and as disclosed and described in U.S. patent application Ser. No. 11/224,060, filed on Sep. 13, 2005 and entitled "Fully-Threaded Bioabsorbable Suture Anchor," the disclosure of which is hereby incorporated by reference in its entirety. In other embodiments, at least one of the two suture anchors may be an Arthrex Biocorkscrew™, disclosed in U.S. Patent Application Publication No. 2004/0106950, the disclosure of which is hereby incorporated by reference in its entirety, having an eyelet and loaded with a single or double strands of sutures.

In an exemplary embodiment, suture anchors 30 have a flexible elongated member 40 (for example, suture 40) preferably attached to a proximal end 42, as illustrated in FIG. 4. One strand of suture 40 from each anchor 30 (preferably opposite colors) is removed. Using a suture retriever instrument 44, one of the four remaining sutures 40 is retrieved through the lateral (or anterolateral) cannula 46 and is passed through the tendon 34 using a suture passer instrument 44. This step is repeated for the three remaining sutures 40 to create a horizontal mattress configuration. When large tears are present, and if desired, all suture strands may be used to obtain additional medial fixation. In this case, the additional strands would be tied and cut.

Figure 5:
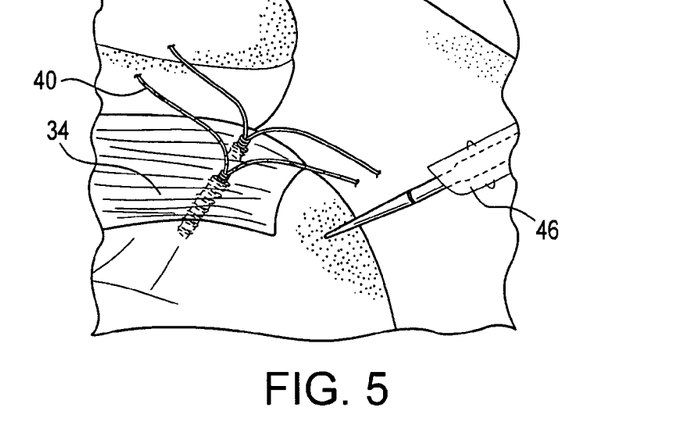
FIG. 5 is a side view of the structure of FIG. 1 and at a step subsequent to that shown in FIG. 4.
Figure 6:
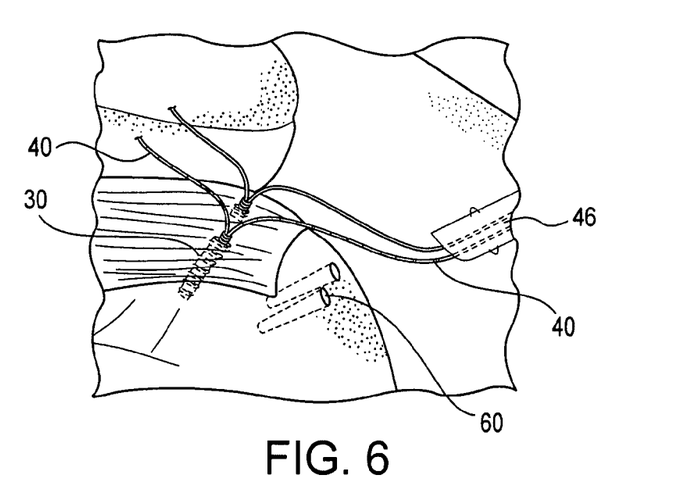
FIG. 6 is a side view of the structure of FIG. 1 and at a step subsequent to that shown in FIG. 5.

Referring now to FIG. 5, the medial row is tied leaving the suture tails 40 uncut. As described below, these suture tails 40 will be draped over the lateral aspect of the tendon 34 and will be held in place with two knotless fixation devices. As also shown in FIGS. 5 and 6, two pilot holes 60 for the knotless fixation devices 62 are formed approximately 5-10 mm distal to the lateral edge of the greater tuberosity using a punch, for example, through the lateral (or anterolateral) cannula 46. In an exemplary embodiment, at least one of the two knotless fixation devices 62 is a fixation device (an Arthrex "PushLock" anchor) as disclosed and described in U.S. Patent Application Publication No. 2004/0093031, the disclosure of which is hereby incorporated by reference in its entirety, or an Arthrex "SwiveLock" anchor as described below with reference to FIGS. 11-13.

As illustrated in FIG. 6, one suture strand 40 from each suture anchor 30 is retrieved through the lateral (or anterolateral) cannula 46. Both suture strands 40 are then threaded through an eyelet 64 of the knotless fixation device 62 (for example, through the eyelet of the PushLock anchor or of the SwiveLock anchor) on the distal end 66 of the driver 68.

Figure 7:
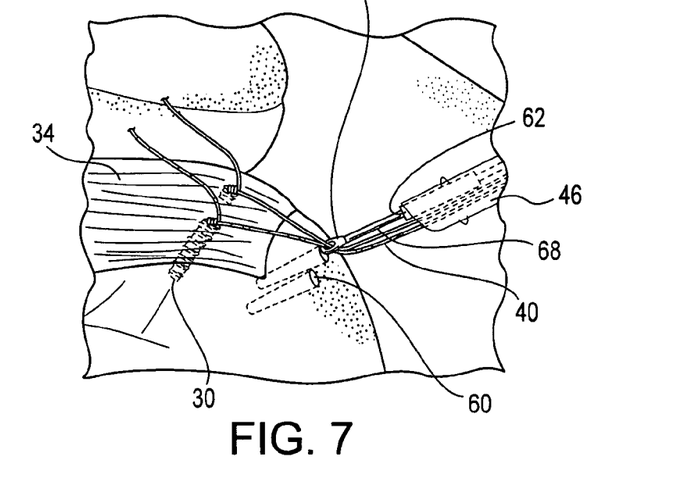
FIG. 7 is a side view of the structure of FIG. 1 and at a step subsequent to that shown in FIG. 6.

Subsequently, and as shown in FIG. 7, the distal tip 66 of the knotless fixation device 62 is brought to the edge of the pilot hole 60 while holding onto the suture tails 40. This will reduce the tendon 34 to its desired position on the footprint. Also, the knot stack from the medial suture anchors 30 is forced to lie flat against the tendon 34 minimizing potential impingement issues from the suture 40.

Figure 8:
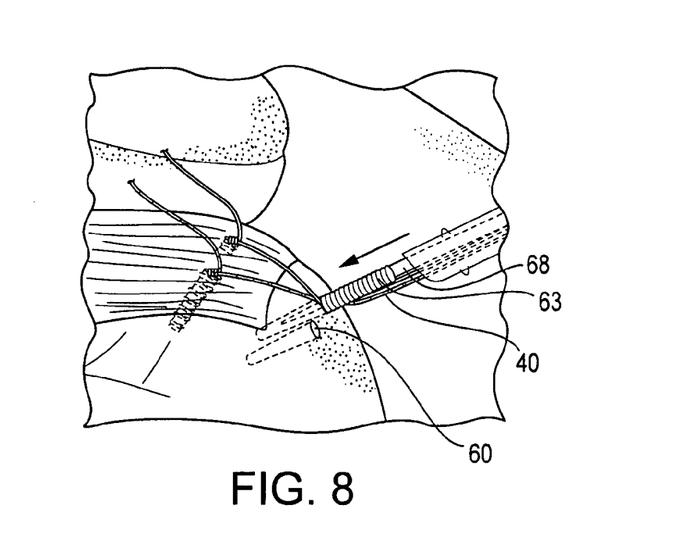
FIG. 8 is a side view of the structure of FIG. 1 and at a step subsequent to that shown in FIG. 7.

The driver 68 is then completely advanced into the pilot hole 60 beyond the first laser line, until the anchor body 63 contacts the bone and the tissue tension is evaluated (FIG. 8). If it is determined that the tension is not adequate, the driver 68 can be backed out and the tension readjusted. Alternatively, additional tension may be applied, while leaving the driver 68 in place, by pulling on each suture strand 40 independently. A mallet 80 may be employed to impact the anchor body 63 into the pilot hole 60 until the second laser line is flush with the humerus.

Figure 9:
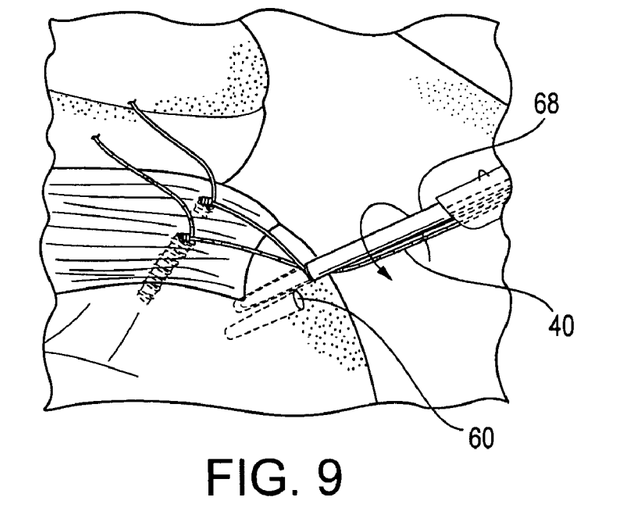
FIG. 9 is a side view of the structure of FIG. 1 and at a step subsequent to that shown in FIG. 8.
Figure 10:
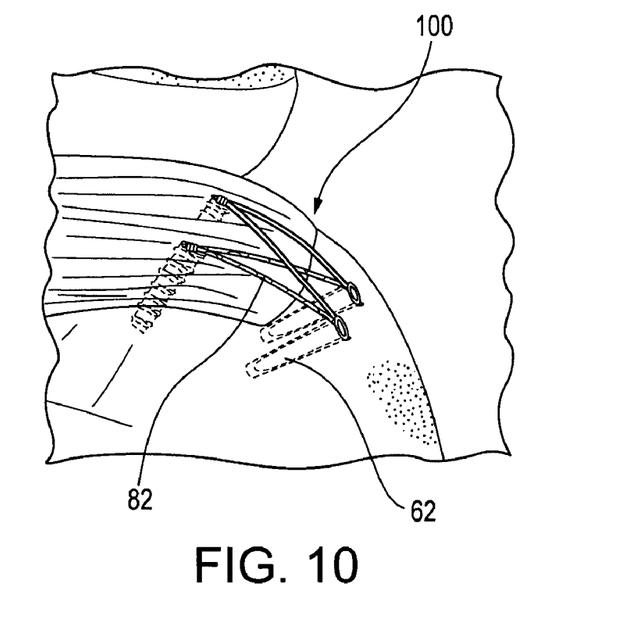
FIG. 10 is a side view of the structure of FIG. 1 and at a step subsequent to that shown in FIG. 9.

Referring now to FIG. 9, the driver 68 is turned counterclockwise to disengage the eyelet (within pilot hole 60) from the driver shaft. The sutures 40 are then cut flush using a suture cutter (not shown). The steps described above with reference to FIGS. 6 through 9 are subsequently repeated for the second knotless fixation device 62 (for example, a second PushLock anchor) to obtain the criss-cross suturing arrangement 82 of FIG. 10 having double rows of fixation devices. The criss-cross suturing arrangement 82, together with the two suture anchors 30 combined with knotless lateral fixation using the two knotless fixation devices 62 form exemplary repair system 100 (FIG. 10) of the present invention.

Figure 11A:
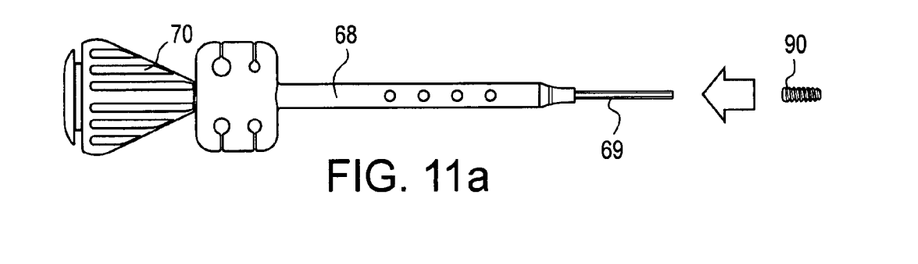
FIGS. 11(a)-(g) illustrate various steps of assembling a driver with a swivel knotless fixation device employed during a knotless repair according to the present invention.
Figure 11B:
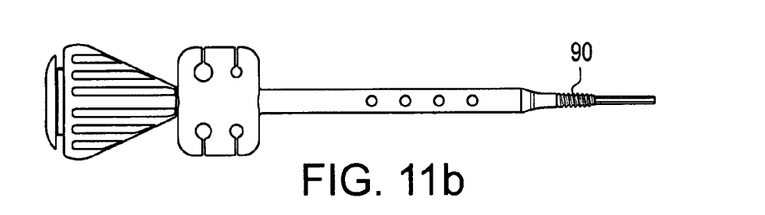
Figure 11C:
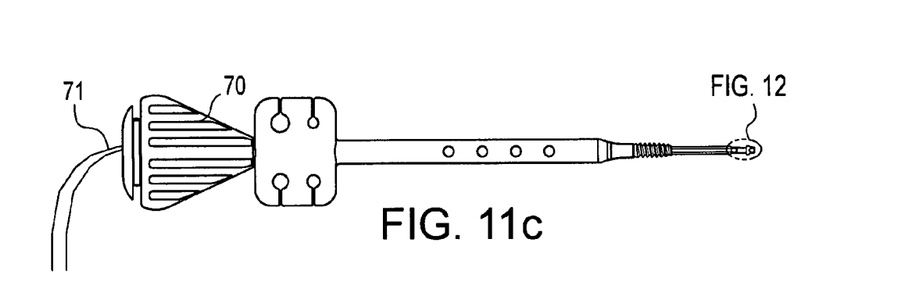
Figure 11D:
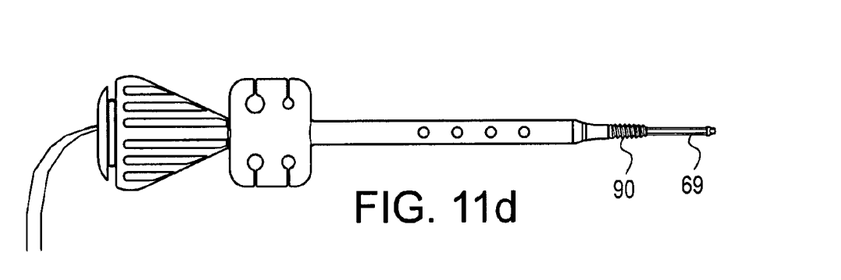
Figure 11E:
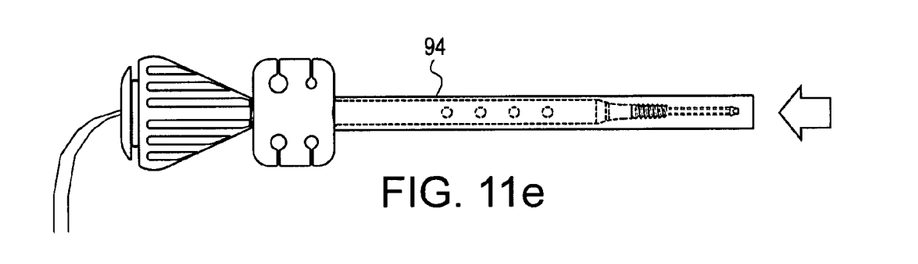
Figure 11F:
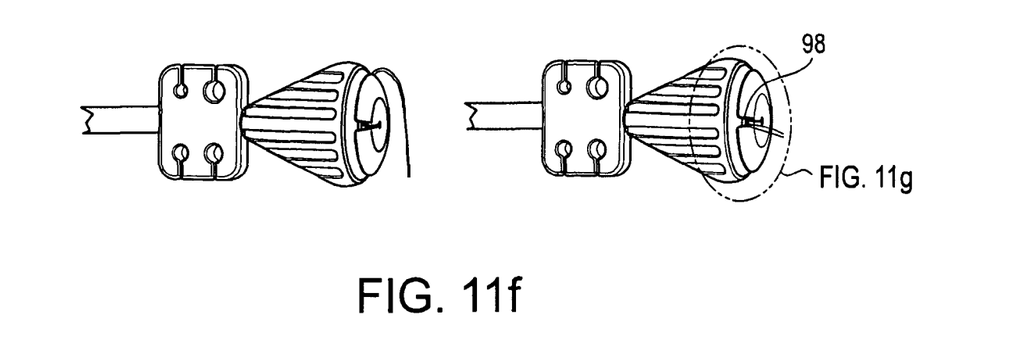
Figure 11G:
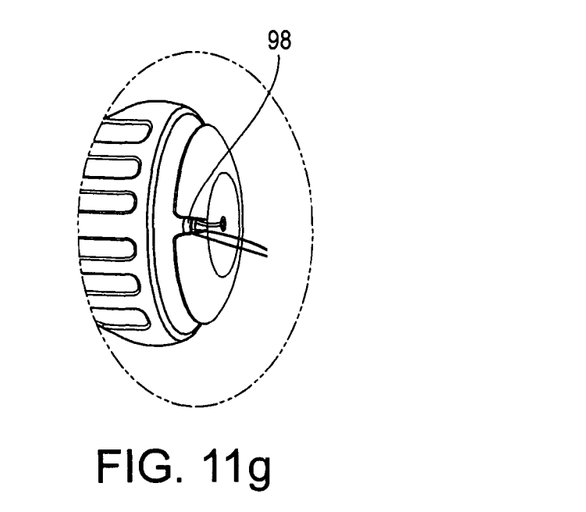
Figure 12:
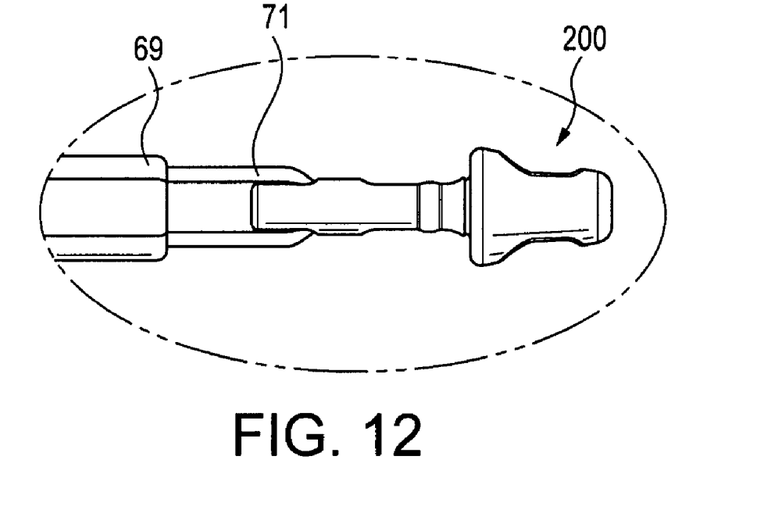
FIG. 12 is a first enlarged side view of the swivel anchor implant illustrated in FIGS. 11(a)-(g).
Figure 13:
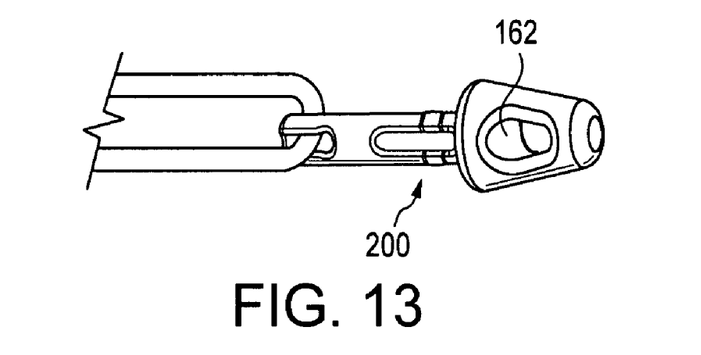
FIG. 13 is a second enlarged side view of the swivel anchor implant of FIG. 12.
Figure 14:
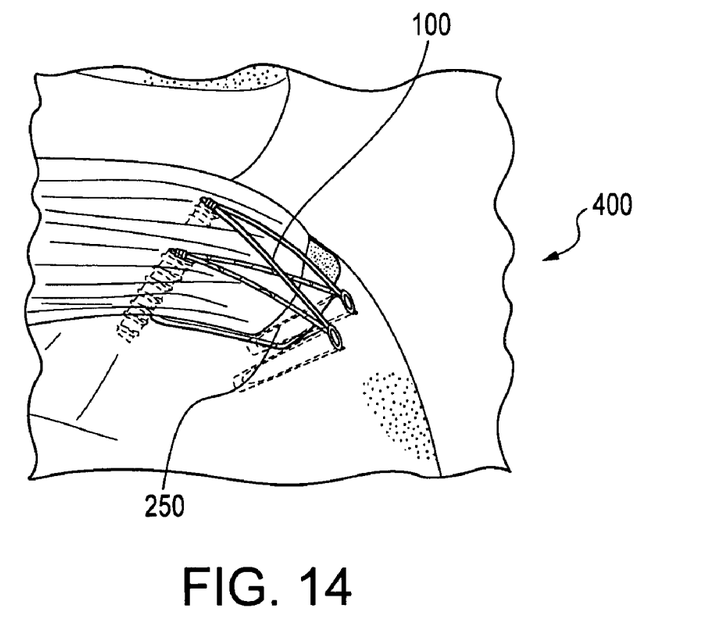
FIG. 14 is a side view of the structure of FIG. 1 according to a second exemplary embodiment of arthroscopic rotator cuff repair of the present invention.
Figure 15:
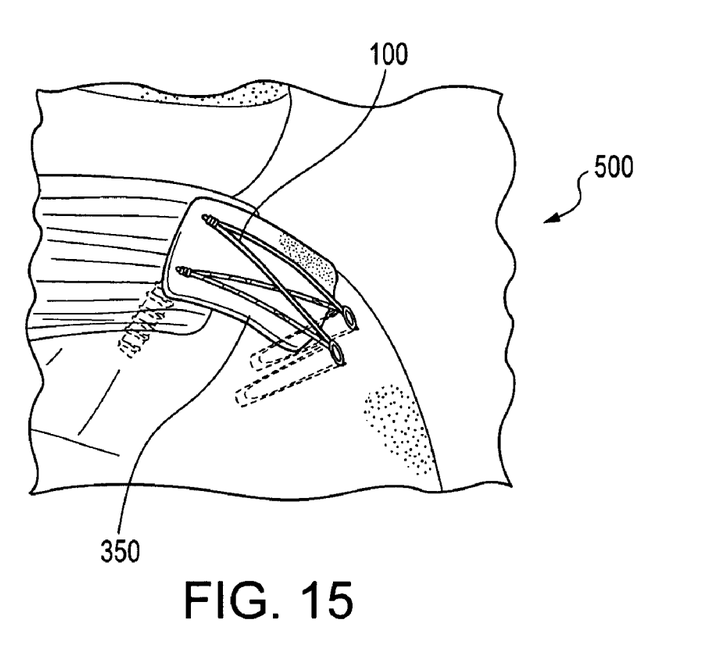
FIG. 15 is a side view of the structure of FIG. 1 according to a third exemplary embodiment of arthroscopic rotator cuff repair of the present invention.

FIGS. 11-13 illustrate exemplary steps of the installation of knotless fixation devices with a swivel anchor implant 200 on driver 68 during a knotless method of attaching tissue to bone according to other embodiments of the present invention. The knotless fixation devices with a swiveling implant 200, are sold by Arthrex, Inc. under the tradename SwiveLock™, and may be used in lieu of the exemplary PushLock anchors described above with reference to the exemplary knotless rotator cuff repair described in FIGS. 1 through 10. The installation technique is similar to the one described above, except that the lateral fixation is accomplished by threading suture through an implant 200 that swivels on the shaft of the driver, and the implant is secured by an anchor that is screwed (by rotating the shaft of the driver), rather than pushed, over the implant.

As shown in FIGS. 11(a)-(f), a driver 68 is used to install the knotless fixation devices with a swiveling implant. Driver 68 features a thin cannulated rod 69 passing slidably and rotatably through a cannulated driver assembly. The tip of thin cannulated rod 69 is adapted to accept swivel anchor implant 200 within the cannulation at its tip, preferably via a snap fit. Cannulated rod 69 has a hexagonal outer surface for receiving anchor body (i.e., a screw) 90 having a corresponding cannulation.

During installation of the knotless anchor having a swiveling implant 200, the screw 90 is first inserted onto cannulated rod 69 of the driver 68. As shown in FIGS. 11(a) and (b), screw 90 is loaded onto rod 69 and then fully seated on the shaft end of the driver. FIG. 11(c) illustrates the swivel anchor implant 200. Traction sutures 71 extending from the proximal end of the swivel anchor implant 200 are threaded through the cannulation of the driver 68 (FIG. 11(c)). Subsequently, the swivel anchor implant 200 is seated on the driver tip and until advanced until it snaps onto place (FIG. 11(d)). A protective tube 94 (FIG. 11(e)) may be placed over the tip of the assembly for shipping purposes. The traction sutures 71 may be looped around the driver handle, as shown in FIGS. 11(f) and (g), and secured in a cleat 98 to prevent the implant 200 from becoming prematurely detached from the driver.

The knotless fixation devices, whether of the first embodiment (PushLock anchors) or the second embodiment (SwivelLock anchors) advantageously minimize or eliminate the need to tie knots. The use of such anchors also provides secure fixation of the suture construct—the secure suture construct results from the suture being pushed into a pilot hole on the lateral row and held tightly by an anchors.

The sutures employed in the method of the present invention may be formed of any flexible material. In the preferred embodiment, the sutures forming the construct are made of a high strength suture material, such as Arthrex FiberWire suture, which is described in U.S. Pat. No. 6,716,234 to Grafton et al., the disclosure of which is incorporated by reference in its entirety. In additional embodiments, the suture strands may be FiberWire sutures of alternating colors to maximize repair strength, aid in suture management and provide superior tying characteristics.

In another preferred embodiment, any flexible elongated member, such as tape, rather than suture, may be employed, to further improve tissue compression, improve fixation in the anchors, and to further hold collagen or bone marrow aspirate better than suture. Preferably, the tape, such as the high strength suture tape disclosed in U.S. Patent Application Publication No. 2005/0192631, the disclosure of which is incorporated by reference herein, is braided and rectangular-like in cross-section. In another preferred embodiment, an allograft or biological component may be used instead of suture or tape. The allograft or biological component may be comprised of tendon or pericardium, for example, which provides improved tissue repair. In yet additional embodiments, any combination of suture, suture tape, and allograft or biological component may be employed, depending on the characteristics of the specific surgical repair and/or as desired.

According to additional exemplary embodiments of the present invention, the present invention may be further employed in conjunction with allograft or porous collagen material that may be optionally hydrated with bone marrow aspirate. In the exemplary embodiments illustrated in FIGS. 14 and 15, repair systems 400, 500 of the present invention comprise, for example, the repair system 100 (described with reference to FIG. 10) and implant material 250, 350 provided arthroscopically (preferably under the tissue prior or above the tissue) prior to implanting the lateral row of the repair system 100.

In exemplary embodiments, implant material 250, 350 may be porous collagen material (BioSponge™) or tendon allograft (AlloBridge™) that can be readily hydrated or impregnated with a hydrating solution comprising aspirated bone marrow. The hydrating solution may consist essentially of bone marrow, preferably consisting essentially of autogenous bone marrow. Alternatively, the hydrating solution may comprise additional elements, such as various growth factors such as hyaluronic acid, antiseptics and/or antibiotics and medicine materials, in addition to or in lieu of the bone marrow. The BioSponge™ 250 (FIG. 14) or AlloBridge™ 350 (FIG. 15) impregnated or hydrated with bone marrow can act as carrier of bone marrow at the repair site, the bone marrow promoting a biological response to damaged tissue and reinforcing the repair of such damaged tissue. The implanted material 250, 350 may be provided at various locations of the repair site (for example, above the tissue, under the tissue, or extending from the tissue) depending upon the characteristics of the repair site and of the damaged tissue.

During the surgical repair, the bone marrow aspirate provides a cell suspension that can be readily processed intraoperatively for immediate implantation. According to exemplary embodiments, the bone marrow aspirate may be withdrawn from the iliac crest or may be aspirated from the femur and humerus. Once the bone marrow aspirate is aspirated (with a syringe, for example) from an aspirate region such as the humeral head, the BioSponge™ or AlloBridge™ is hydrated with the bone marrow and then the hydrated BioSponge™ or AlloBridge™ is provided arthroscopically (for example, under the tissue) prior to implanting the lateral row implants of system 100. Alternatively, or additionally, bone marrow aspirate may be injected directly or localized to a repair site, to facilitate healing.

The bodies of the fixation devices of the present invention may be preferably formed of a translucent or transparent polymer material, and are preferably made of bioabsorbable materials such as polyglycolic or polylactic acid polymers.

Although the present invention has been described in relation to particular embodiments thereof, many other variations and modifications and other uses will become apparent to those skilled in the art. Accordingly, it is not intended that the present invention be limited to the illustrated embodiments, but only by the appended claims.

What is claimed as new and desired to be protected by Letters Patent of the United States is:

1. A knotless method of attaching soft tissue to bone, comprising:
providing a first medial row constructed with a first plurality of fixation devices, wherein the at least one of the first plurality of fixation devices is an anchor;
providing a second lateral row constructed with a second plurality of fixation devices, wherein the at least one of the second plurality of fixation devices is a knotless fixation device, the knotless fixation device comprising a cannulated interference device and an implant containing an aperture, the aperture being configured to capture a flexible member; and
passing the flexible member through the soft tissue and over a lateral portion of the soft tissue, the flexible member being attached at one end to the anchor and secured at an opposite end in a hole in bone by the knotless fixation device without tying a knot, wherein the step of passing the flexible member further comprises:
passing the flexible member through the aperture of the implant;
inserting the flexible member and the implant into the hole; and advancing the cannulated interference device toward a proximal end of the implant, to engage and lock in the implant with the flexible member in the hole.

2. The method of claim 1, further comprising the formation of a structure of multiple passes of said flexible member over the soft tissue, wherein the structure is held in place by the fixation devices in the first and second rows.

3. The method of claim 2, wherein the flexible member of the structure is comprised of suture.

4. The method of claim 2, wherein the flexible member of the structure is comprised of tape.

5. The method of claim 2, wherein the flexible member of the structure is comprised of an allograft or biological component.

6. The method of claim 2, further comprising the step of providing an implant material adjacent to the structure of multiple passes.

7. The method of claim 6, wherein the step of providing an implant material further comprises:
providing aspirate bone marrow;
providing a material to be implanted in the vicinity of a repair site defined by at least the structure of multiple passes;
hydrating the material with aspirate bone marrow to form the implant material; and
securing the implant material at the repair site.

8. The method of claim 6, wherein the implant material is selected from the group consisting of collagen, allograft and bone marrow.

9. The method of claim 8, wherein the implant material is porous collagen impregnated with autogenous bone marrow.

10. The method of claim 8, wherein the implant material is tendon allograft impregnated with autogenous bone marrow.

11. A knotless method of attaching soft tissue to bone, comprising:
inserting a first anchor through the soft tissue, wherein the first anchor comprises a length of an elongated flexible member secured to the first anchor prior to insertion;
inserting the first anchor into the bone;
passing the length of the elongated flexible member over the soft tissue; and
securing, after said step of passing, the length of the elongated flexible member to a second anchor, wherein the second anchor is a knotless fixation device comprising a cannulated interference device and an implant containing an aperture, the aperture being configured to capture the elongated flexible member, and wherein the step of securing the elongated flexible member further comprises:
passing the elongated flexible member through the aperture of the implant;
inserting the elongated flexible member and the implant into the hole; and
advancing the cannulated interference device toward a proximal end of the implant, to engage and lock in the implant with the elongated flexible member in the hole.

12. The method of claim 11, wherein said step of securing the length of the elongated flexible member comprises, in order:
inserting the second anchor with the length of the elongated flexible member coupled thereto into the bone;
tensioning the length of the elongated flexible member; and
securing the length of the elongated flexible member to the second anchor.

13. The method of claim 12, wherein the step of inserting the second anchor comprises inserting the anchor directly into the bone without the anchor passing through the soft tissue.

14. The method of claim 11, wherein the step of securing the elongated flexible member to the second anchor is performed without tying any knots.

15. The method of claim 11, wherein the second anchor is a press-in suture anchor.

16. The method of claim 11, wherein the second anchor is a suture anchor with a swivel implant.

17. A knotless method of attaching soft tissue to bone, the method comprising:
inserting a first, second, and third anchor into the bone;
fixedly securing a first length of a flexible elongated member over the soft tissue to the first and second anchors; and
fixedly securing a second length of the flexible elongated member over the soft tissue to the first and third anchors, wherein at least one of the first and third anchors is a knotless fixation device comprising a cannulated interference device and an implant containing an aperture, the aperture being configured to capture the second length of the elongated flexible member, and wherein the step of securing the elongated flexible member further comprises:
passing the second length of the elongated flexible member through the aperture of the implant;
inserting the second length of the elongated flexible member and the implant into the hole; and
advancing the cannulated interference device toward a proximal end of the implant, to engage and lock in the implant with the second length of the elongated flexible member in the hole.

18. The method of claim 17, wherein the first anchor is positioned beneath the soft tissue and the second and third anchors are positioned laterally to the soft tissue.

19. The method of claim 17, wherein the first and second lengths of the elongated flexible member are fixedly secured to the first anchor prior to insertion into the bone.

20. A knotless method of attaching soft tissue to bone, comprising:
inserting a first anchor with a length of an elongated flexible member attached thereto through the soft tissue;
inserting the first anchor into the bone;
inserting a second anchor with no suture attached thereto into bone;
passing the length of the elongated flexible member over the soft tissue; and
fixedly securing the length of the elongated flexible member to the inserted second anchor.

21. The method of claim 20, further comprising, after inserting the first anchor into the bone, fixedly securing the attached length of the elongated flexible member to the first anchor.

22. The method of claim 20, wherein the step of fixedly securing the attached length of the elongated flexible member to the first anchor is performed without tying any knots.

23. The method of claim 20, further comprising the step of tensioning the elongated flexible member prior to the step of fixedly securing the elongated flexible member to the first anchor.

24. The method of claim 23, wherein the step of tensioning the flexible elongated member comprises grasping the length of the flexible elongated member and pulling.

25. A method of attaching soft tissue to bone, comprising:
providing a first medial row constructed with a first plurality of fixation devices, wherein the at least one of the first plurality of fixation devices is an anchor;
providing a second lateral row constructed with a second plurality of fixation devices, wherein the at least one of the second plurality of fixation devices is a knotless fixation device comprising a cannulated interference device and an implant containing an aperture, the aperture being configured to capture a flexible member;
providing an implant material adjacent the first medial row and adjacent the soft tissue;
providing the flexible member attached to the first medial row; and
passing the flexible member through the soft tissue and over a lateral portion of the soft tissue to form a structure of multiple passes of said flexible member over the soft tissue, wherein the step of forming the structure of multiple passes further comprises:
passing the flexible member through the aperture of the implant;
inserting the flexible member and the implant into the hole; and
advancing the cannulated interference device toward a proximal end of the implant, to engage and lock in the implant with the flexible member in the hole.

26. The method of claim 25, wherein the implant material is porous collagen impregnated with autogenous bone marrow.

27. The method of claim 25, wherein the implant material is tendon allograft impregnated with autogenous bone marrow.

28. The method of claim 1, wherein the implant is a swivel implant.

29. The method of claim 1, further comprising the steps of:
preloading the cannulated interference device of the knotless fixation device on a shaft of a driver; and
inserting the cannulated interference device into the hole.

* * * * *

(12) EX PARTE REEXAMINATION CERTIFICATE (206th)

Ex Parte Reexamination Ordered under 35 U.S.C. 257

United States Patent
ElAttrache et al.

(10) Number: US 8,012,174 C1
(45) Certificate Issued: Feb. 9, 2022

(54) METHOD FOR DOUBLE ROW FIXATION OF TENDON TO BONE

(75) Inventors: Neal S. ElAttrache, Los Angeles, CA (US); James E. Tibone, Los Angeles, CA (US)

(73) Assignee: ARTHREX, INC., Naples, FL (US)

Supplemental Examination Request:
No. 96/000,357, May 5, 2021

Reexamination Certificate for:
Patent No.: 8,012,174
Issued: Sep. 6, 2011
Appl. No.: 11/700,916
Filed: Feb. 1, 2007

Related U.S. Application Data (60) Provisional application No. 60/763,915, filed on Feb. 1, 2006.

(51) Int. Cl.
*A61F 2/08* (2006.01)
*A61B 17/04* (2006.01)

(52) U.S. Cl.
CPC ........ *A61B 17/0401* (2013.01); *A61F 2/0811* (2013.01); *A61B 2017/044* (2013.01); *A61B 2017/0409* (2013.01); *A61B 2017/0414* (2013.01)

(58) Field of Classification Search
None
See application file for complete search history.

(56) References Cited

To view the complete listing of prior art documents cited during the supplemental examination proceeding and the resulting reexamination proceeding for Control Number 96/000,357, please refer to the USPTO's public Patent Application Information Retrieval (PAIR) system under the Display References tab.

*Primary Examiner* — Glenn K Dawson (57) ABSTRACT

A system and method for soft tissue to bone repair employing at least one suture anchor combined with at least one knotless fixation device. The method for soft tissue to bone fixation includes: (i) providing a first medial row constructed with a first plurality of fixation devices, at least one of the first plurality of fixation devices is an anchor; and (ii) providing a second lateral row constructed with a second plurality of fixation devices, at least one of the second plurality of fixation devices is a knotless fixation device, and suture or tape or allograft/biological component extending over the soft tissue and secured in place by the anchors in the first and second medial rows.

US 8,012,174 C1

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE
SPECIFICATION AFFECTED BY AMENDMENT
ARE PRINER HEREIN.

Figure 6A:
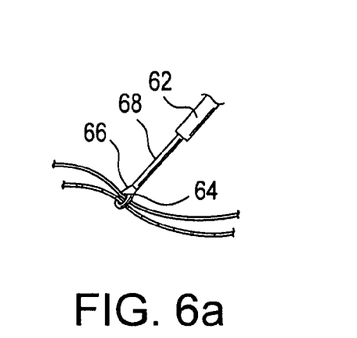

Column 2, after after line 20 and before line 21:

*FIG. 6a is a partial perspective view of the end of a driver and knotless fixation device according to the present invention.*

Figure 8A:
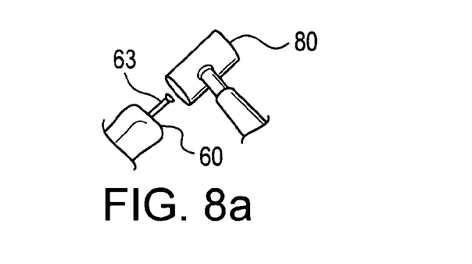

Column 2, after line 24 and before line 25:

*FIG. 8a is a partial perspective view of a mallet used in the method of repair according to the present invention.*

AS A RESULT OF REEXAMINATION, IT HAS BEEN DETERMINED THAT:

Claims 11-14 and 20-22 are cancelled.

Claims 1, 15-17, 23 and 25 are determined to be patentable as amended.

Claims 2, 3, 18, 24, 28 and 29, dependent on an amended claim, are determined to be patentable.

New claims 30-39 are added and determined to be patentable.

Claims 4-10, 19, 26 and 27 were not reexamined.

1. [A knotless] *An arthroscopic* method of attaching soft tissue to bone *with knotless fixation*, comprising:
   providing a first medial row constructed with a first plurality of fixation devices, wherein [the] *at least one of the first plurality of fixation devices* is an anchor;
   providing a second lateral row constructed with a second plurality of fixation devices, wherein [the] *at least one of the second plurality of fixation devices* is a knotless fixation device, the knotless fixation device comprising a cannulated interference device and an implant containing an aperture, the aperture being configured to capture a flexible member; and
   passing the flexible member through the soft tissue and over a lateral portion of the soft tissue, the flexible member [being] *comprising a suture tail* attached at one end to the anchor and secured at an opposite end in a hole in bone by the knotless fixation device without tying a knot, *such that the securing of the suture tail at the opposite end in the hole in bone is knotless*,
   wherein the step of passing the flexible member *over the lateral portion of the soft tissue* further comprises:
      *retrieving the flexible member through a cannula after the flexible member is attached to the anchor;*
      *after retrieving the flexible member through the cannula,* passing the flexible member through the aperture of the implant *by threading the suture tail through the aperture of the implant*;
      *after passing the flexible member through the aperture of the implant,* inserting the flexible member and the implant, *with the suture tail threaded through the aperture of the implant,* into the hole; and
      advancing the cannulated interference device toward a proximal end of the implant, to engage and lock in the implant with *suture tail of* the flexible member in the hole.

15. The method of claim [11] *1*, wherein the [second anchor] *knotless fixation device* is a press-in suture anchor.

16. The method of claim [11] *1*, wherein the [second anchor] *knotless fixation device* is a suture anchor with a swivel implant.

17. [A knotless] *An arthroscopic* method of attaching soft tissue to bone *with knotless fixation*, the method comprising:
   inserting a first, second, and third anchor into the bone;
   fixedly securing a first length of a flexible elongated member over the soft tissue to the first and second anchors; and
   fixedly securing a second length of the flexible elongated member over the soft tissue to the first and third anchors, wherein at least one of the first and third anchors is a knotless fixation device comprising a cannulated interference device and an implant containing an aperture, the aperture being configured to capture the second length of the elongated flexible member, and wherein the step of *fixedly* securing the *second length of the* elongated flexible member further comprises:
      retrieving the second length of the elongated flexible member through a cannula;
      after retrieving the second length of the elongated flexible member through the cannula, passing the second length of the elongated flexible member through the aperture of the implant;
      after passing the elongated flexible member through the aperture of the implant, inserting the second length of the elongated flexible member and the implant, with the second length threaded through the aperture of the implant, into [the] *a* hole *in bone*; and
      advancing the cannulated interference device toward a proximal end of the implant, to engage and lock in the implant with the second length of the elongated flexible member in the hole, *such that the step of fixedly securing the second length of the flexible elongated member in the hole is knotless*.

23. The method of claim [20] *17*, further comprising the step of tensioning the elongated flexible member prior to the step of [fixedly securing the elongated flexible member to the anchor] *advancing the cannulated interference device*.

25. [A] *An arthroscopic* method of attaching soft tissue to bone, comprising:
   providing a first medial row constructed with a first plurality of fixation devices, wherein the at least one of the first plurality of fixation devices is an anchor;
   providing a second lateral row constructed with a second plurality of fixation devices, wherein the at least one of the second plurality of fixation devices is a knotless fixation device comprising a cannulated interference device and an implant containing an aperture, the aperture being configured to capture a flexible member;
   providing [an implant] *a material to be implanted, the material being provided* adjacent the first medial row and adjacent the soft tissue;
   providing the flexible member attached to the first medial row; and passing the flexible member through the soft tissue and over a lateral portion of the soft tissue to form a structure of multiple passes of said flexible member over the soft tissue, wherein the step of forming the structure of multiple passes further comprises:
retrieving the flexible member through a cannula;
after retrieving the flexible member through the cannula, passing the flexible member through the aperture of the implant;
after passing the flexible member through the aperture of the implant, inserting the flexible member and the implant, *with the flexible member threaded through the aperture of the implant,* into a hole in bone; and
advancing the cannulated interference device toward a proximal end of the implant, to engage and lock in the implant with the flexible member in the hole.

30. *The method of claim 1, further comprising, prior to advancing the cannulated interference device toward the proximal end of the implant, tensioning the flexible member by pulling on the suture tail threaded through the aperture of the implant.*

31. *The method of claim 1, further comprising the step of cutting the flexible member flush to the bone, such that the opposite end of the suture tail is secured in the hole in bone.*

32. *The method of claim 17, further comprising, prior to advancing the cannulated interference device toward the proximal end of the implant, tensioning the flexible member by pulling on the second length threaded through the aperture of the implant.*

33. *The method of claim 17, further comprising the step of cutting the flexible member flush to the bone, such that the second length thereof is secured in the hole in bone.*

34. *A knotless method of attaching soft tissue to bone, comprising:*
*providing a first medial row constructed with a first plurality of fixation devices, wherein at least one of the first plurality of fixation devices is an anchor;*
*providing a second lateral row constructed with a second plurality of fixation devices, wherein at least one of the second plurality of fixation devices is a knotless fixation device, the knotless fixation device comprising a cannulated interference device and an implant containing an aperture, the aperture being configured to capture a flexible member; and*
*passing the flexible member through the soft tissue and over a lateral portion of the soft tissue, the flexible member being attached at a medial side to the anchor and secured at a lateral side in a hole in bone by the knotless fixation device without tying a knot,*
*wherein the step of passing the flexible member over the lateral portion of the soft tissue further comprises:*
*retrieving the flexible member through a cannula after the flexible member is attached to the anchor;*
*after retrieving the flexible member through the cannula, passing the flexible member through the aperture of the implant by threading the lateral side of the flexible member through the aperture of the implant;*
*after passing the flexible member through the aperture of the implant, inserting the flexible member and the implant, with the flexible member threaded through the aperture of the implant, into the hole; and*
*advancing the cannulated interference device toward a proximal end of the implant, to engage and lock in the implant with the flexible member in the hole.*

35. *The method of claim 34, further comprising, prior to advancing the cannulated interference device toward the proximal end of the implant, tensioning the flexible member by pulling on the flexible member threaded through the aperture of the implant.*

36. *The method of claim 34, further comprising the step of cutting the flexible member flush to the bone, such that the lateral side of the flexible member is secured in the hole in bone.*

37. *A knotless method of attaching soft tissue to bone, the method comprising:*
*inserting a first, second, and third anchor into the bone;*
*fixedly securing a first length of a flexible elongated member over the soft tissue to the first and second anchors; and*
*fixedly securing a second length of the flexible elongated member over the soft tissue to the first and third anchors, wherein at least one of the first and third anchors is a knotless fixation device comprising a cannulated interference device and an implant containing an aperture, the aperture being configured to capture the second length of the elongated flexible member, and wherein the step of fixedly securing the second length of the elongated flexible member further comprises:*
*retrieving the second length of the elongated flexible member through a cannula;*
*after retrieving the second length of the elongated flexible member through the cannula, passing the second length of the elongated flexible member through the aperture of the implant;*
*after passing the elongated flexible member through the aperture of the implant, inserting the second length of the elongated flexible member and the implant, with the second length threaded through the aperture of the implant, into a hole in bone; and*
*advancing the cannulated interference device toward a proximal end of the implant to engage and lock in the implant with the second length of the elongated flexible member in the hole.*

38. *The method of claim 37, further comprising, prior to advancing the cannulated interference device toward the proximal end of the implant, tensioning the flexible member by pulling on the second length threaded through the aperture of the implant.*

39. *The method of claim 37, further comprising the step of cutting the flexible member flush to the bone, such that the second length thereof is secured in the hole in bone.*

\* \* \* \* \*